(12) United States Patent
Day et al.

(10) Patent No.: US 7,501,523 B2
(45) Date of Patent: Mar. 10, 2009

(54) METHOD FOR PREPARING CUCURBITURILS

(75) Inventors: Anthony Ivan Day, Captains Flat (AU); Alan Peter Arnold, Flynn (AU); Rodney John Blanch, Holt (AU)

(73) Assignee: NewSouth Innovations Pty Limited, Sydney, NSW (AU)

( * ) Notice: Subject to any disclaimer, the term of this patent is extended or adjusted under 35 U.S.C. 154(b) by 0 days.

(21) Appl. No.: 10/571,707

(22) PCT Filed: Sep. 10, 2004

(86) PCT No.: PCT/AU2004/001232

§ 371 (c)(1),
(2), (4) Date: Mar. 13, 2006

(87) PCT Pub. No.: WO2005/026168

PCT Pub. Date: Mar. 24, 2005

(65) Prior Publication Data
US 2007/0066818 A1    Mar. 22, 2007

(30) Foreign Application Priority Data
Sep. 12, 2003   (AU) .............................. 2003905037

(51) Int. Cl.
C07D 403/02   (2006.01)
(52) U.S. Cl. ................................... 548/303.4
(58) Field of Classification Search ............... 548/303.4
See application file for complete search history.

(56) References Cited

U.S. PATENT DOCUMENTS

| | | | |
|---|---|---|---|
| 2,654,763 A | 10/1953 | Adkins et al. | |
| 3,203,960 A | 8/1965 | Gandon et al. | |
| 3,252,901 A | 5/1966 | Zettler et al. | |
| 6,365,734 B1 | 4/2002 | Kim et al. | |
| 6,639,069 B2 | 10/2003 | Kim et al. | |
| 6,793,839 B1 | 9/2004 | Day et al. | |
| 6,869,466 B2 | 3/2005 | Day et al. | |
| 6,939,973 B1 * | 9/2005 | Rebek et al. ............. | 548/303.4 |
| 2002/0133003 A1 | 9/2002 | Kim et al. | |
| 2003/0212268 A1 | 11/2003 | Kim et al. | |
| 2004/0265237 A1 | 12/2004 | Kim et al. | |

FOREIGN PATENT DOCUMENTS

| | | |
|---|---|---|
| DE | 4001 139 | 10/1990 |
| EP | 1 094 065 | 4/2001 |
| WO | WO-00/68232 | 5/2000 |
| WO | WO-03/004500 | 1/2003 |
| WO | WO-03/024978 | 3/2003 |
| WO | WO 03/055888 | 7/2003 |
| WO | WO-2004/072151 | 8/2004 |
| WO | WO-2005/003136 | 1/2005 |
| WO | WO-2005/003391 | 1/2005 |
| WO | WO-2005/010004 | 2/2005 |
| WO | WO-2005/010058 | 2/2005 |
| WO | WO-2005/087777 | 9/2005 |
| WO | WO-2005/090351 | 9/2005 |
| WO | WO-2005/103053 | 11/2005 |

OTHER PUBLICATIONS

Day et al., J. Org. Chem., 2001, v. 66, p. 8094-8100.*
Day, et al., "Contolling factors in the synthesis of cucurbituril and its homoluges", J. Org. Chem. (2001), vol. 66, pp. 8094-8100.
Lee, J.W. et al., "Cucurbituril homologues and derivatives: new opportunities in supramolecular, chemistry", Accounts of Chemical Research (2003), vol. 36, pp. 621-630.
Kim, J. et al. New cucurbituril homologues: syntheses, isolation, characterization, and X-ray crystal structures of cucurbit . . . , J.Am. Chem. Soc (2000), vol. 122, pp. 540-541.
Isobe, H. et al., "synthesis of disubstituted cucurbit[6]uril and its rotaxane derivative", Organic Letters (202), vol. 4, No. 8, pp. 1387-1289.
Behrend, R. et al, "Ueber Condensationsproducte aus Glycoluril und Formaldehyd", 1905, pp. 1-37, Justus Leibig's Annalen der Chemie.
Freeman, W.A. et al, "Cucurbituril", J. Am. Chem. Soc., 103 1981, pp. 7397-7368.
Flinn, A. et al, "Decaethylcucurit[5]uril", Angew. Chem. Int. Ed. Engl., 1992, pp. 1475-1477, vol. 31, No. 1.
Dantz, D.A. et al "Complexation of volatile organic molecules from the gas phase with cucurbituril and β-cyclodextrin", 1998, pp. 79-83, vol. 9, No. 2, Supramolecular Chemistry.
Elemans, J.A.A.W. et al, "Bipyridine functionalized molecular chips. Self-assembly of their ruthenium complexes in water" Abstract No. 129:183422, 1998, Chemical Abstracts.
Buschmann, H.J. et al, :Cucurbituril as a ligand for the complexation of cations in aqueous solutions, 193, 1992, pp. 93-97, Inorganic Chimica Acta.
Mock, W.L. et al, "Topics in Current Chemistry", 175, 1995, pp. 1-24.

* cited by examiner

Primary Examiner—Kamal A Saeed
Assistant Examiner—Robert Havlin
(74) Attorney, Agent, or Firm—Stephen J. Weyer; Stites & Harbison PLLC

(57) ABSTRACT

The invention relates to a method for preparing cucurbiturils. The method comprises reacting an oligomer consisting of 2 to 11 linked glycolurils or glycoluril analogues with one or more compounds selected from glycoluril, glycoluril analogues and/or oligomers of glycoluril or glycoluril analogues, in the presence of an acid, to form a cucurbituril. The method can be used to prepare variably substituted cucurbiturils having specific substituted units at specific locations in the cucurbituril. The invention also provides cucurbiturils prepared by the method of the invention. The invention further provides novel cucurbiturils.

17 Claims, No Drawings

METHOD FOR PREPARING CUCURBITURILS

FIELD OF THE INVENTION

The present invention relates to a method for preparing cucurbit[4 to 12]urils.

BACKGROUND TO THE INVENTION

Cucurbiturils are a class of macrocyclic compounds based on oligomers of glycoluril or glycoluril analogues.

"Cucurbituril" is the name given to the cyclic oligomer formed by linking six (6) glycoluril molecules via methylene bridges. However, the term "cucurbituril" has also been used, and is used in this specification, to refer to a class of compounds. To avoid confusion, the compound cucurbituril is referred to in this specification as "unsubstituted cucurbit[6]uril".

Unsubstituted cucurbit[6]uril was first described in the literature in 1905 in a paper by R. Behrend, E. Meyer and F. Rusche (Leibigs Ann. Chem., 339, 1, 1905). The macrocyclic structure of unsubstituted cucurbit[6]uril was first described in 1981 by W. A. Freeman et. al. ("Cucurbituril", J. Am. Chem. Soc., 103 (1981), 7367-7368). Unsubstituted cucurbit[6]uril has a chemical formula of $C_{36}H_{36}N_{24}O_{12}$ and is a macrocyclic compound having a central cavity.

The substituted cucurbituril decamethylcucurbit[5]uril was first synthesised and identified in 1992 by Flinn et. al. (Angew. Chem. Int. Ed. Engl., 1992, 31, 1475).

Various unsubstituted and substituted cucurbit[4 to 12]urils were synthesised by Day et. al. as described in the applicant's international patent application no. PCT/AU00/00412 (WO 00/68232), incorporated herein by reference.

WO 00/68232 describes the preparation of various cucurbit[4 to 12]urils from glycoluril, substituted glycolurils, or a mixture of glycoluril and substituted glycolurils. WO 00/68232 also describes the preparation of cucurbit[4 to 12]urils from a diether analogue of glycoluril, or a mixture of a diether analogue of glycoluril and glycoluril (Example 2 and Example 122). All the methods for preparing cucurbit[n]urils described in WO 00/68232 comprise reacting glycoluril and/or one or more glycoluril analogues to form the cucurbituril.

A class of cucurbit[4 to 20]urils and methods for preparing these cucurbit[4 to 20]urils are also described in U.S. Pat. No. 6,365,734. All the methods for preparing cucurbit[4 to 12]urils described in U.S. Pat. No. 6,365,734 comprise reacting glycoluril to form unsubstituted cucurbit[4 to 20]urils, or reacting substituted glycoluril to form substituted cucurbit[4 to 20]urils where all the units of the formula (B) as defined below making up the cucurbit[4 to 20]uril are identical.

Most of the cucurbiturils described in the prior art are unsubstituted or uniformly substituted cucurbiturils, that is, cucurbiturils where all the units of the formula (B) as defined below making up the cucurbituril are identical. The methods for preparing cucurbiturils described in WO 00/68232 can be used to prepare "variably substituted cucurbiturils" as defined below. If the methods for preparing cucurbit[n]urils described in WO 00/68232 are used to prepare "variably substituted cucurbiturils" as defined below, a large number of different variably substituted cucurbiturils are typically produced. For example, in Example 122(2) of WO 00/68232 cucurbit[s,u]urils were formed where s and u are 1,4; 2,3; 3,2; 4,1; 1,5; 2,4; 3,3; 4,2; 5,1; 1,6; 2,5; 3,4; 4,3; 5,2; 6,1.

Cucurbit[n]urils comprise a rigid central cavity with two portals to the central cavity. These portals are surrounded by polar groups and are narrower in diameter than the internal diameter of the cavity.

Cucurbit[4 to 12]urils selectively complex various molecules. For example, the central cavity selectively encapsulates gases and volatile molecules. Cucurbit[4 to 12]urils can also selectively form complexes with molecules at the polar ends of the central cavity. Cucurbit[4 to 12]urils can be used to form complexes with, and then later release, gases, volatiles, and other molecules. These properties give cucurbit[4 to 12]urils a wide variety of uses. These uses include for example:

- entrapment and removal of pollutants,
- use as odourisers, releasing fragrances slowly over time,
- to trap unpleasant odours or toxic vapours, and
- a chemical purification or separation techniques, for example, in chromatographic columns.

It would be advantageous to provide alternative methods for preparing cucurbit[4 to 12]urils.

SUMMARY OF THE INVENTION

The present inventors have found that for many uses of cucurbit[4 to 12]urils, it is desirable to use "variably substituted cucurbiturils", that is, cucurbit[4 to 12]urils in which the units of the formula (B) as defined below making up the cucurbituril are not identical.

The inventors have found that the number and type of groups at $R^1$, $R^2$, $R^3$ and/or $R^5$ in the units of the formula (B) making up the cucurbit[4 to 12]uril, and the relative location of those groups within the cucurbituril, alters the solubility of the cucurbituril. For example, tetramethylcucurbit[2,4]uril has greater solubility in water than unsubstituted cucurbit[6]uril. The inventors have also found that the number and type of groups at $R^1$, $R^2$, $R^3$ and/or $R^5$ in the units of the formula (B) making up the cucurbit[4 to 12]uril affects the extent to which the cucurbituril forms complexes with other compounds. For example, the inventors have found the association constant of methane is three times higher for dimethylcucurbit[1,4]uril than for decamethylcucurbit[5]uril., and the association constant of dioxane in unsubstituted cucurbit[6]uril is two times higher than in tetramethylcucurbit[2,4]uril. To prepare a cucurbituril having the desired solubility together with the desired complexing properties for a particular application, it may be necessary to prepare a cucurbituril having particular groups at $R^1$, $R^2$, $R^3$ and $R^5$ at particular relative positions in the cucurbituril.

Further, for some applications, it is desirable to use variably substituted cucurbit[4 to 12]urils where only one or a few of the $R^1$ or $R^2$ groups in the cucurbituril is other than H, so that the cucurbituril has a similar ability to-form complexes as an unsubstituted cucurbituril of the same degree of polymerisation but has a particular number and location of substituents that can react with other compounds, for example, to bind the cucurbituril to a solid support or to bind the cucurbituril to another cucurbituril.

The methods for preparing cucurbit[4 to 12]urils described in WO 00/68232 can be used to prepare certain variably substituted cucurbit[4 to 12]urils. However, when variably substituted cucurbit[4 to 12]urils are prepared by the methods described in WO 00/68232, a large number of different substituted cucurbiturils may be produced resulting in low yields of the desired variably substituted cucurbituril. For some applications, the desired variably substituted cucurbituril may need to be separated from the mixture of cucurbiturils produced, prior to the use of the variably substituted cucurbituril.

The inventors have therefore found that it would be advantageous to provide a method for preparing cucurbit[4 to 12]urils which allows a greater degree of control over the relative position of particular groups at $R^1$, $R^2$, $R^3$ and $R^5$ in the cucurbituril compared to prior art methods for preparing cucurbiturils. The inventors have in addition found such a method.

In one aspect, the present invention provides a method for preparing a cucurbit[n]uril, the method comprising the steps of:
(a) mixing
(1) a compound of the formula (1)

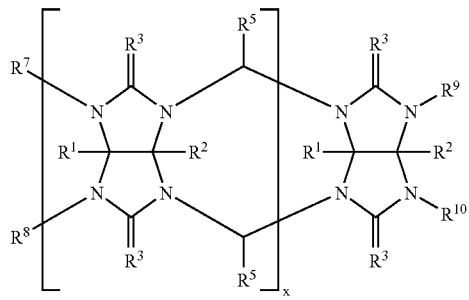

(1)

wherein:
for each unit of the formula (A)

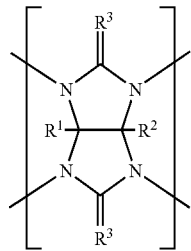

(A)

in the compound,
$R^1$ and $R^2$ may be the same or different and are each a univalent radical, or
$R^1$, $R^2$ and the carbon atoms to which they are bound together form an optionally substituted cyclic group, or
$R^1$ of one unit of the formula (A) and $R^2$ of an adjacent unit of the formula (A) together form a bond or a divalent radical, and
each $R^3$ is independently selected from the group consisting of =O, =S, =NR, =CXZ, =CRZ and =CZ$_2$, wherein Z is an electron withdrawing group such as —NO$_2$, —CO$_2$R, —COR, —CN or —CX$_3$, X is halo, and R is H, an optionally substituted straight chain, branched or cyclic, saturated or unsaturated hydrocarbon radical, or an optionally substituted heterocyclyl radical;
each $R^5$ is independently selected from the group consisting of H, alkyl and aryl;
$R^7$ and $R^8$ may be the same or different and are independently selected from the group consisting of H and —CHR$^5$OR$^5$, or $R^7$ and $R^8$ together form the group —CHR$^5$—O—CHR$^5$—, where each $R^5$ is independently selected and is as defined above;
$R^9$ and $R^{10}$ may be the same or different and are independently selected from the group consisting of H and —CHR$^5$OR$^5$, or $R^9$ and $R^{10}$ together form the group —CHR$^5$—O—CHR$^5$—, where each $R^5$ is independently selected and is as defined as above; and
x is an integer from 1 to 10;
(2) one or more compounds of the formula (2)

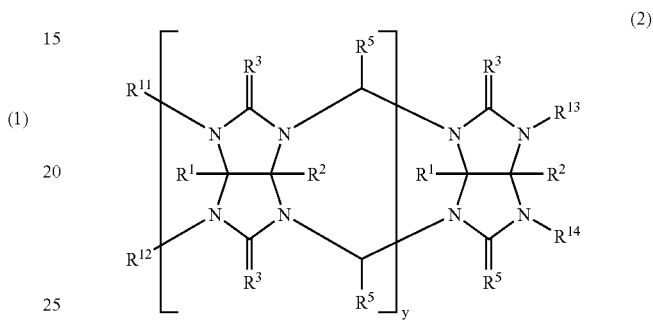

(2)

wherein $R^1$, $R^2$, $R^3$ and $R^5$ are as defined above for formula (1);
$R^{11}$ and $R^{12}$ may be the same or different and are independently selected from the group consisting of H and —CHR$^5$OR$^5$, or $R^{11}$ and $R^{12}$ together form the group —CHR$^5$—O—CHR$^5$—, where each $R^5$ is independently selected and is as defined above;
$R^{13}$ and $R^{14}$ may be the same or different and are independently selected from the group consisting of H and —CHR$^5$OR$^5$, or $R^{13}$ and $R^{14}$ together form the group —CHR$^5$—O—CHR$^5$—, where each $R^5$ is independently selected and is as defined as above; and
y is 0 or an integer from 1 to 9 and x+y=10 or less; and
(3) an acid;

to form a mixture; and
(b) exposing the mixture to conditions effective for the compound of the formula (1) and the one or more compounds of the formula (2) to form a cucurbit[n]uril.

In another aspect, the present invention provides a cucurbit[n]uril prepared by the method of the present invention.

As will be apparent to a person skilled in the art, $R^1$ and $R^2$ may be selected from a very broad range of substituents. The present invention is not limited to methods where $R^1$ and $R^2$ are particular groups.

When $R^1$ and $R^2$ are univalent radicals, $R^1$ and $R^2$ are typically independently selected from the group consisting of —R, —OR, —NR$_2$ where each R is independently selected, —NO$_2$, —CN, —X, —COR, —COX, —COOR,

where each R is independently selected,

where each R is independently selected, —SeR, —SiR$_3$
where each R is independently selected, —SR, —SOR,

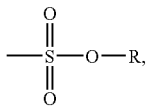

—SO$_2$R, —S—S—R, —BR$_2$ where each R is independently selected, —PR$_2$ where each R is independently selected,

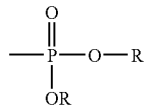

where each R is independently selected,

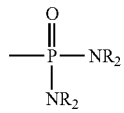

where each R is independently selected, —P$^+$R$_2$ where each R is independently selected and a metal or metal complex, wherein R is H, an optionally substituted straight chain, branched or cyclic, saturated or unsaturated hydrocarbon radical, or an optionally substituted heterocyclyl radical, and X is halo. In some embodiments, R is H, an optionally substituted C$_{1-10}$ alkyl, an optionally substituted C$_{2-10}$ alkenyl, or an optionally substituted C$_{5-10}$ aryl.

The method of the present invention may produce a mixture of two or more different cucurbiturils. In accordance with the present invention, at least one of the cucurbiturils is formed from at least one compound of formula (1) and at least one of each of the compounds of formula (2). In some embodiments, at least some of the cucurbit[n]urils produced by the method of the present invention are formed from one compound of formula (1) and one of each of the compounds of formula (2). In some embodiments, at least some of the cucurbit[n]urils produced by the method of the present invention are formed from more than one compound of formula (1) and one of each of the compounds of formula (2), or from one compound of formula (1) and more than one of each of the compounds of formula (2).

Typically at least one of the one or more compounds of the formula (2) is different to the compound of the formula (1).

Typically R$^7$=R$^8$, R$^9$=R$^{10}$, R$^{11}$=R$^{12}$ and R$^{13}$=R$^{14}$.

Typically step (a) comprises adding the compound of the formula (1) to the one or more compounds of the formula (2) and mixing, and then mixing the compounds with the acid. However, in some embodiments of the invention, the compound of the formula (1) is mixed with the acid, and the resultant mixture then added to the one or more compounds of the formula (2). Alternatively, in some embodiments of the invention, one or more of the compounds of the formula (2) is mixed with the acid, and the compound of the formula (1) and the remaining compounds of the formula (2), if any, are then added and mixed.

Typically step (b) comprises heating the mixture to a temperature of from 20° C. to 120° C. for a period of time sufficient for the compound of formula (1) and the one or more compounds of formula (2) to form a cucurbit[n]uril.

In some embodiments, step (b) further comprises incorporating into the mixture one or more compounds that can form bridges of the formula —CHR$^5$— between compounds of formula (1) and (2). As will be apparent to a person skilled in the art, the compound that can form bridges of the formula —CHR$^5$—, forms these bridges by reaction with, or replacement of, the groups R$^7$ to R$^{14}$ to form bridges of the formula —CHR$^5$— bound to the nitrogen atoms to which R$^7$ to R$^{14}$ were bound. Such a compound can be incorporated into the mixture by adding the compound to the mixture. Alternatively, the compound can be mixed with the compound of formula (1), the one or more compounds of formula (2) and/or the acid, prior to all these components being mixed together to form the mixture.

As will be apparent to a person skilled in the art, in some embodiments of the invention, it is not necessary to include a compound that can form bridges of the formula —CHR$^5$— between compounds of formula (1) and (2) in the mixture in order to form a cucurbituril in step (b) of the method of the present invention. For example, if all the groups R$^7$, R$^8$, R$^9$, R$^{10}$, R$^{11}$, R$^{12}$, R$^{13}$ and R$^{14}$ in the compounds of formula (1) and (2) in the mixture are other than H, then the compounds of formula (1) and (2) can react to form a cucurbit[n]uril without the presence of such a compound.

However, if all of the groups R$^7$, R$^8$, R$^9$, R$^{10}$, R$^{11}$, R$^{12}$, R$^{13}$ and R$^{14}$ are H then such a compound must be included in the mixture in order for the compounds of formula (1) and (2) to form a cucurbit[n]uril.

Typically, if the molar ratio of the groups R$^7$, R$^8$, R$^9$, R$^{10}$, R$^{11}$, R$^{12}$, R$^{13}$ and R$^{14}$ in the compounds of formula (1) and (2) in the mixture which are H to those which are not H is greater than 1, then a compound that can form bridges of the formula —CHR$^5$— between compounds of formula (1) and (2) is included in the mixture.

In another aspect, the present invention provides a cucurbit[n]uril of the formula:

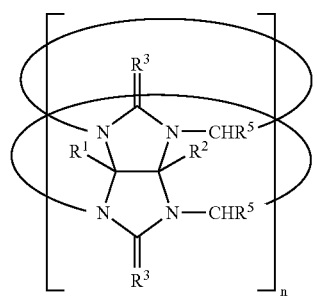

wherein:
for each unit of the formula (B):

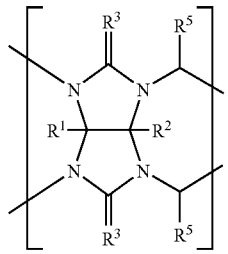

(B)

in the cucurbit[n]uril,

R¹ and R² may be the same or different and are each a univalent radical, or

R¹, R² and the carbon atoms to which they are bound together form an optionally substituted cyclic group, or R¹ of one unit of the formula (B) and R² of an adjacent unit of the formula (B) together form a bond or a divalent radical, each R³ is independently selected from the group consisting of =O, =S, =NR, =CXZ, =CRZ and =CZ$_2$, wherein Z is an electron withdrawing group, X is halo and R is H, an optionally substituted straight chain, branched or cyclic, saturated or unsaturated hydrocarbon radical, or an optionally substituted heterocyclyl radical, and each R⁵ is independently selected from the group consisting of H, alkyl and aryl;

and n is an integer from 4 to 12, and wherein at least one R³ in the cucurbit[n]uril is =CXZ, =CRZ or =CZ$_2$.

Definitions

Having regard to the cucurbiturils described in WO 00/68232 and U.S. Pat. No. 6,365,734 and the inventors' further work, the class of cucurbiturils is broader than that described in either of WO 00/68232 or U.S. Pat. No. 6,365,734.

As used herein, the term "cucurbituril" refers to a compound of the formula (C):

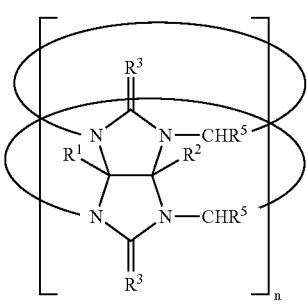

(C)

wherein:
for each unit of the formula (B):

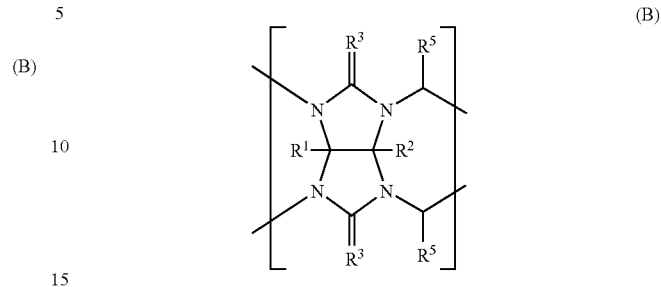

(B)

in the compound,

R¹ and R² may be the same or different and are each a univalent radical, or

R¹, R² and the carbon atoms to which they are bound together form an optionally substituted cyclic group, or R¹ of one unit of the formula (B) and R² of an adjacent unit of the formula (B) together form a bond or a divalent radical, each R³ is independently selected from the group consisting of =O, =S, =NR, =CXZ, =CRZ and =CZ$_2$, wherein Z is an electron withdrawing group such as —NO$_2$, —CO$_2$R, —COR, —CN or —CX$_3$, X is halo and R is H, an optionally substituted straight chain, branched or cyclic, saturated or unsaturated hydrocarbon radical, or an optionally substituted heterocyclyl radical, and each R⁵ is independently selected from the group consisting of H, alkyl and aryl;

and n is the degree of polymerisation, that is, the number of units of the formula (B) in the compound.

When R¹ and R² are univalent radicals, R¹ and R² are typically independently selected from the group consisting of —R, —OR, —NR² where each R is independently selected, —NO$_2$, —CN, —X, —COR, —COX, —COOR,

where each R is independently selected,

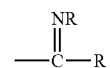

where each R is independently selected, —SeR, —SiR$_3$ where each R is independently selected, —SR, —SOR,

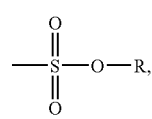

—SO$_2$R, —S—S—R, —BR$_2$ where each R is independently selected, —PR$_2$ where each R is independently selected,

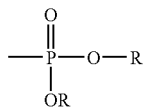

where each R is independently selected,

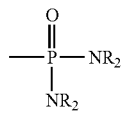

where each R is independently selected, —P⁺R₂ where each R is independently selected and a metal or metal complex, wherein R is H, an optionally substituted straight chain, branched or cyclic, saturated or unsaturated hydrocarbon radical, or an optionally substituted heterocyclyl radical, and X is halo.

To differentiate various cucurbiturils, the inventors have adopted the term "cucurbit[n]uril", where n is the degree of polymerisation of the cucurbituril, that is, the number of units of the formula (B) in the macrocyclic ring of the cucurbituril. For example, a cyclic oligomer comprising eight units of the formula (B) joined together would be denoted as cucurbit[8]uril.

The present invention relates to cucurbit[n]urils where n is an integer from 4 to 12. Unless otherwise specified, the terms "cucurbituril" and "cucurbit[n]uril" as used herein refer to a cucurbit[n]uril where n is an integer from 4 to 12.

As used herein, the terms "unsubstituted cucurbituril" and "unsubstituted cucurbit[n]uril" refer to a cucurbituril in which $R^3$ is =O, and $R^1$, $R^2$ and $R^5$ are H, in all the units of formula (B) in the cucurbituril.

As used herein, the terms "variably substituted cucurbituril" and "variably substituted cucurbit[n]uril" refer to a cucurbituril in which the units of the formula (B) making up the cucurbituril are not all identical.

A variably substituted cucurbit[n]uril may consist of some unsubstituted units of the formula (B) where $R^3$ is =O and $R^1$, $R^2$ and $R^5$ are H, and some substituted units of the formula (B) where $R^3$ is other than =O and/or one or more of $R^1$, $R^2$ and $R^5$ is other than H. To differentiate such compounds, the term "cucurbit[s,u]uril" is used, where s equals the number of substituted units of the formula (B) and u equals the number of unsubstituted units of the formula (B), and s plus u equals n.

To indicate the relative location of the substituted units of the formula (B) in a variably substituted cucurbit[n]uril, a Greek letter is used with α being assigned to a substituted unit of the formula (B) given first priority and all other units of the formula (B) in the macrocyclic ring of the cucurbit[n]uril are assigned a Greek letter in alphabetical order. For example, a cucurbit[6]uril having two units of the formula (B) substituted by X and Y respectively, where the substituted units of the formula (B) are located at opposite sides of the cucurbituril, would be identified by the name αX, δY-cucurbit[2,4]uril. The following representation illustrates such a cucurbit[6]uril when viewed towards one of the portals of the cucurbituril:

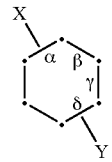

As used herein, the term "glycoluril analogue" refers to a compound of the formula (5):

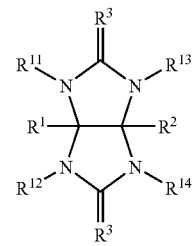

(5)

wherein $R^1$ and $R^2$ may be the same or different and are each a univalent radical, or $R^1$, $R^2$ and the carbon atoms to which they are bound together form an optionally substituted cyclic group, and $R^3$ and $R^{11}$ to $R^{14}$ are as defined above for formula (2).

Typically, when $R^1$ and $R^2$ are univalent radicals, $R^1$ and $R^2$ are independently selected from the group consisting of —R, —OR, —SR, —NR² where each R is independently selected, —NO₂, —CN, —X, —COR, —COX, —COOR,

where each R is independently selected,

where each R is independently selected, —SeR, —SiR₃ where each R is independently selected, —SR, —SOR,

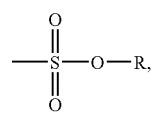

—SO₂R, —S—S—R, —BR₂ where each R is independently selected, —PR₂ where each R is independently selected,

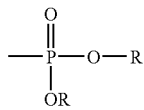

where each R is independently selected,

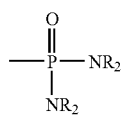

where each R is independently selected, —P$^+$R$_2$ where R is independently selected and a metal or metal complex, wherein R is H, an optionally substituted straight chain, branched or cyclic, saturated or unsaturated hydrocarbon radical, or an optionally substituted heterocyclyl radical, and X is halo.

DETAILED DESCRIPTION OF PREFERRED EMBODIMENTS

Various cucurbit[4 to 12]urils of formula (C) as defined above are novel. In particular, cucurbit[4 to 12]urils of formula (C) where:
1. one or more of the R$^3$ groups in the cucurbituril is other than =O, =S or =NH; or
2. each of the R$^3$ groups in the cucurbituril is =O, =S or =NH, at least one of the R$^3$ groups is =S or =NH, and not all the R$^1$, R$^2$, R$^3$ or R$^5$ groups in the cucurbituril are the same; or
3. each of the R$^3$ groups in the cucurbituril is =O, =S or =NH, one or more of the R$^5$ groups in the cucurbituril is other than H, and not all of the R$^1$, R$^2$, R$^3$ or R$^5$ groups in the cucurbituril are the same;

are not disclosed in the prior art.

The method of the present invention involves preparing cucurbiturils using at least one compound comprising two or more units of the formula (A) joined by bridges of the formula —CHR$^5$— (the compound of formula (1)). As this compound comprises two or more units of the formula (A), the particular R$^1$, R$^2$, R$^3$ and R$^5$ groups in the compound have a fixed position relative to each other which is retained in the cucurbiturils prepared from that compound. Thus the method of the present invention when used to prepare variably substituted cucurbiturils, results in the production of a lesser variety of different variably substituted cucurbit[n]urils than the prior art methods which comprise reacting glycoluril analogues to form cucurbiturils. Accordingly, the method of the present invention allows a greater degree of control over the types of substituted cucurbiturils produced than the prior art methods for preparing cucurbiturils.

As will be apparent to a person skilled in the art, if the groups R$^7$, R$^8$, R$^9$, R$^{10}$, R$^{11}$, R$^{12}$, R$^{13}$ and R$^{14}$ in the compounds of formula (1) and (2) are other than hydrogen, the compounds of formula (1) and (2) can react with each other to form a cucurbituril in step (b) of the method. However, if all of these groups are H, or if, in the compounds of formula (1) and (2) that are to form the cucurbituril, the total number of these groups which are H is greater than the total number which are not H, then a compound that can form bridges of the formula —CHR$^5$— between compounds of formula (1) and (2) must be included in the mixture in order for the compound of formula (1) and the one or more compounds of formula (2) to form a cucurbituril in step (b) of the method.

In formulas (1), (2), (3), (4) and (5), when R$^1$ and R$^2$ are univalent radicals, R$^1$ and R$^2$ may for example be selected from H, an optionally substituted alkyl (e.g. methyl, ethyl, propyl, isopropyl, n-butyl, sec-butyl, isobutyl, tert-butyl, etc), optionally substituted alkenyl, optionally substituted alkynyl, optionally substituted heterocyclyl or optionally substituted aryl (e.g. phenyl, naphthyl, pyridyl, furanyl or thiophenyl), —OR, —SR or —NR$^2$.

In some embodiments, when R$^1$ and R$^2$ are univalent radicals, R$^1$ and R$^2$ include less than 30 carbon atoms. R$^1$ and R$^2$ may for example be selected from the group consisting of alkyl groups of 1 to 30 carbon atoms, alkenyl groups of 1 to 30 carbon atoms, cyclic hydrocarbon groups of 5 to 30 carbon atoms, cyclic groups of 4 to 30 carbon atoms with one or more heteroatoms such as O, N or S, aryl groups of 6 to 30 carbon atoms, and aryl groups of 5 to 30 carbon atoms with one or more hetero atoms such as O, N or S.

R$^1$ and R$^2$ may for example be an alkoxy group such as methoxy, ethoxy, propyloxy etc. R$^1$ and R$^2$ may also be a hydroxy, halo, cyano, nitro, amino, alkylamino or alkylthio radical.

Examples of optionally substituted cyclic groups formed by R$^1$, R$^2$ and the carbon atoms to which they are bound, include optionally substituted saturated or unsaturated cyclic hydrocarbon groups of 5 to 30 carbon atoms, and optionally substituted saturated or unsaturated cyclic groups of 3 to 30, typically 4 to 30, carbon atoms with one or more heteroatoms such as O, N or S.

When R$^1$ and R$^2$ of adjacent units of the formula (A) in the compound of formula (1) or formula (2), or adjacent units of the formula (B) in a cucurbituril, together form a divalent radical, the divalent radical may for example, be a divalent optionally substituted straight chain or branched, saturated or unsaturated hydrocarbon radical comprising 1 or more carbon atoms. The divalent radical may consist of or contain one or more heteroatoms such as O, N or S.

When R is an optionally substituted hydrocarbon radical or an optionally substituted heterocyclyl radical, the hydrocarbon radical or the heterocyclyl radical may be substituted by one or more substituents. Similarly, when R$^1$, R$^2$ and the carbon atoms to which they are bound form together form an optionally substituted cyclic group, the cyclic group may be substituted by one or more substituents. The optional substituents can be any group and may for example be an optionally substituted alkyl, an optionally substituted alkenyl, an optionally substituted alkynyl, an optionally substituted heterocyclyl, an optionally substituted aryl, halo (e.g. F, Cl, Br or I), hydroxyl, alkoxyl, carbonyl, acyl halide, nitro, carboxylic acid, carboxylic acid ester, amino, imino, cyano, isocyanate, thiol, thiol-ester, thio-amide, thio-urea, sulfone, sulfide, sulfoxide or sulfonic acid group or a metal or metal complex. The optional substituent may also be a borane, a phosphorous containing group such as a phosphine, alkyl phosphine, phosphate or phosphoramide, a silicon containing group or a selenium containing group.

Typically Z is selected from the group consisting of —NO$_2$, —CO$_2$R, —COR, —CN and —CX$_3$, where X is halo (e.g. F, Cl, Br or I) and R is H, alkyl (for example, methyl, ethyl, propyl, etc), alkenyl, alkynyl, aryl, heteroaryl or saturated or unsaturated heterocyclyl.

The compound that can form bridges of the formula —CHR$^5$—between compounds of formula (1) and (2) is typically selected from a compound of the formula R$^5$COR$^5$ or a compound of the formula $R^5OC(R^5)_2OR^5$, where $R^5$ is as defined above and each $R^5$ group is independently selected, trioxane, optionally substituted 3,4-dihydropyran or optionally substituted 2,3-dihydrofuran. The optionally substituted 3,4-dihydropyran or optionally substituted 2,3-dihydrofuran may be substituted by groups such as alkyl, alkenyl, alkynyl, aryl or halo. The compound of the formula $R^5COR^5$ may for example be formaldehyde.

$R^5$ is H, alkyl or aryl. When $R^5$ is alkyl, $R^5$ is typically a $C_{1-5}$ alkyl, such as methyl, ethyl, propyl, iso-propyl, butyl, sec-butyl, tert-butyl etc. When $R^5$ is aryl, $R^5$ may for example be phenyl.

The majority of cucurbit[4 to 12]urils prepared to date are cucurbit[4 to 12]urils wherein $R^3$ is =O and $R^5$ is H in all units of the formula (B) making up the cucurbituril.

In one embodiment, the present invention provides a method for preparing such a cucurbit[4 to 12]uril, the method comprising the steps of:

(a) mixing (1) a compound of the formula (3)

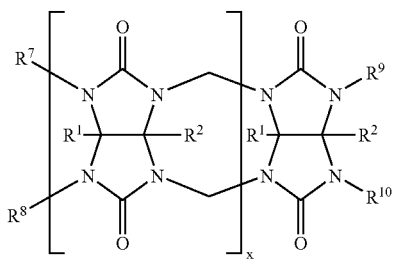

(3)

wherein:
for each unit of the formula (D):

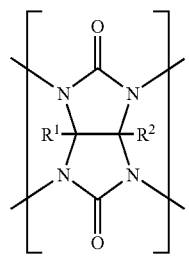

(D)

in the compound, $R^1$ and $R^2$ may be the same or different and are each a univalent radical, or $R^1$, $R^2$ and the carbon atoms to which they are bound together form an optionally substituted cyclic group, or $R^1$ of one unit of the formula (D) and $R^2$ of an adjacent unit of the formula (D) together form a bond or a divalent radical;

$R^7$ and $R^8$ may be the same or different and are independently selected from the group consisting of H and —CH$_2$OH, or $R^7$ and $R^8$ together form the group —CH$_2$—O—CH$_2$—;

$R^9$ and $R^{10}$ may be the same or different and are independently selected from the group consisting of H and —CH$_2$—OH, or $R^9$ and $R^{10}$ together form the group —CH$_2$—O—CH$_2$—;

and x is an integer from 1 to 10;

(2) one or more compounds of the formula (4)

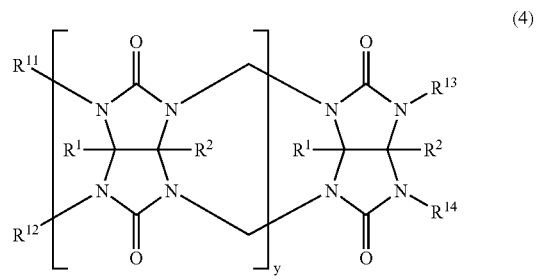

(4)

wherein:
$R^1$ and $R^2$ are as defined above for formula (3);

$R^{11}$ and $R^{12}$ may be the same or different and are independently selected from the group consisting of H and —CH$_2$OH, or $R^{11}$ and $R^{12}$ together form the group —CH$_2$—O—CH$_2$—;

$R^{13}$ and $R^{14}$ may be the same or different and are independently selected from the group consisting of H and —CH$_2$OH, or $R^{13}$ and $R^{14}$ together form the group —CH$_2$—O—CH$_2$—;

and y is 0 or an integer from 1 to 9 and x+y=10 or less; and (3) an acid;

to form a mixture; and (b) exposing the mixture to conditions effective for the compound of the formula (1) and the one or more compounds of the formula (2) to form a cucurbit[n]uril.

In such an embodiment of the invention, if a compound that can form bridges of the formula —CHR$^5$— between the compounds of formula (4) and (5) is used, the compound is selected from formaldehyde, paraformaldehyde, trioxane, 2,3-dihydropyran or 2,3-dihydrofuran.

Typically the mixture formed in step (a) of the method of the present invention further comprises a templating compound. As used herein, the term "templating compound" refers to a compound that affects the relative amount of cucurbit[n]urils of differing degrees of polymerisation prepared by the method of the present invention. For example a templating compound when added to the mixture, may alter the ratio of, say, cucurbit[5]uril to cucurbit[6]uril, when that ratio is compared with that ratio of cucurbit[5]uril to cucurbit[6]uril that is produced using mixtures not containing a templating compound or containing a different templating compound, but otherwise reacted under identical conditions.

Typically, the templating compound is a salt. However, it has been found that many other compounds can also act as a templating compound.

Any compound that can alter the ratio of cucurbiturils of different degrees of polymerisation prepared by the method of the present invention can be used as the templating compound. The templating compound may be an organic compound, a salt of an organic compound, or an inorganic compound. Suitable compounds that may be used as a templating compound include ammonium chloride, lithium chloride, sodium chloride, potassium chloride, rubidium chloride, caesium chloride, ammonium bromide, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoanaline, taurine, blue tetrazolium, 2-amino-3-methyl benzoic acid, indol-3-aldehyde, cysteine, 4-acetamidoaniline, p-aminophenol, acetamide, 4-aminoacetophenone, 4-dimethylaminobezaldehyde, 2-aminobenzimidazol, bis-(4,4'-bipyridyl)-α,α'-xylene, red phosphorus, and lithium p-toluenesulfonate. The present inventors believe that a large number of other compounds could be suitable for use as templating compounds and therefore the above list should not be considered to be exhaustive. The anions of the acid may also be considered to be a templating compound.

The templating compounds may be added singly to the reaction mixture, or two or more templating compounds may be added to the reaction mixture.

If a salt is used as the templating compound, the salt is preferably a metal halide, ammonium halide, metal sulphate or metal tosylate. It-is preferred that the anion of the salt corresponds to the anion of the acid used. For example, where the acid used is hydrochloric acid, a metal chloride or ammonium chloride is a preferred salt. Similarly, iodide-containing salts are preferably used when the acid is hydriodic acid, and bromide-containing salts are preferably when the acid is hydrobromic acid.

The acid is preferably a strong mineral acid or a strong organic acid. In principle, any acid can be used. The acid acts to catalyse the reactions taking place.

Preferred acids include sulfuric acid, hydrochloric acid, hydrobromic acid, hydriodic acid, deuterated sulfuric acid, phosphoric acid, p-toluenesulfonic acid, and methane sulphonic acid. It will be appreciated that this list is not exhaustive and that any acid that can catalyse the reaction may be used in the method of the present invention.

It is preferred that the acid has a concentration of at least 5M. It is also preferred that the concentration of the acid in the mixture comprising the compound of formula (1), the one or more compounds of formula (2) and the acid, is at least 5M.

Typically the mixture is not an anhydrous mixture.

The mixture may further comprise a solvent. The solvent may for example be selected from trifluoroacetic acid, methanesulfonic acid, 1,1,1-trifluorethanol or an ionic liquid.

Step (b) of the method of the present invention typically comprises heating the mixture to a temperature of from 20° C. to 120° C. for a period of time sufficient for the compound of the formula (1) and the one or more compounds of the formula (2) to form a cucurbit[n]uril. Typically the temperature is 60° C. to 110° C., most preferably from 80° C. to 110° C. It is preferred that boiling of the mixture is avoided. Heating under reflux is not required but may be used. It has been found that the mixture should be generally heated to a temperature of 60° C. and above to produce cucurbit[n]urils, with increased yields being obtained at temperatures in the range of 80° C. to 100° C.

Preparation of Compounds of Formula (1) and (2)

(a) Substituted Glycolurils and Glycoluril Analogues

Formula (2) encompasses glycoluril analogues of the formula (5) as defined above.

Formula (5) encompasses glycoluril of the formula:

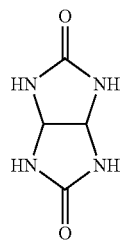

Formula (5) also encompasses substituted glycolurils of the formula:

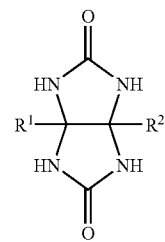

There are a large number of substituted glycolurils known in the literature. Particular reference is made to the review article by Harro Petersen in Synthesis, 1973, 249-293, incorporated herein by reference. That review article contains a list of about 30 substituted glycolurils. The literature since that article has disclosed several other examples of substituted glycolurils and it is believed that essentially any α- or β-diketone could be used to make a substituted or unsubstituted glycoluril.

Further substituted glycolurils are disclosed in WO 00/68232.

Glycoluril analogues can be prepared by methods known in the art, for example as described in the review article by Harro Petersen in Synthesis, 1973, 249-293

Glycoluril analogues can for example be prepared as described in the following reaction schemes:

Scheme 1

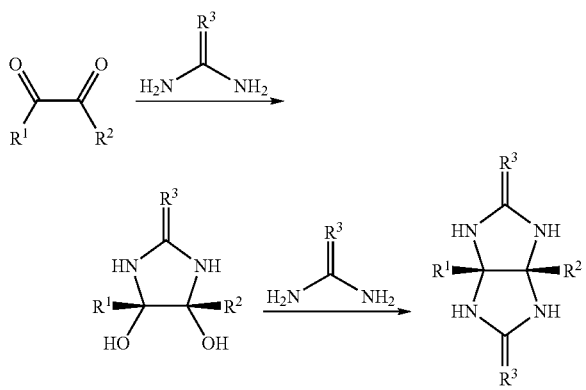

Scheme 2

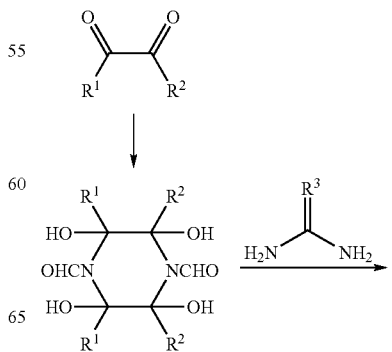

-continued

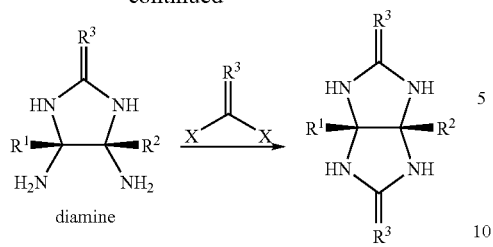
diamine wherein each R¹, R² and R³ group is independently selected and is as defined above for formula (2), and X is a leaving group such as a halo or a thioether.

The reactions of Scheme 1 may be carried out under the following conditions:
a) Reaction in water at room temperature for several days;
b) Reaction in acidic water with or without a cosolvent;
c) Reaction in a hydrocarbon solvent in the presence of an acid catalyst while water of reaction is removed azeotropically;
d) Reaction in a hydrocarbon solvent in the presence of a Lewis acid with or without removal of water generated during reaction.

Scheme 1 can, for example, be used to prepare the following substituted glycolurils (in compound 1.2, X is halo). These compounds are new, and form a further aspect of the present invention.

1.1
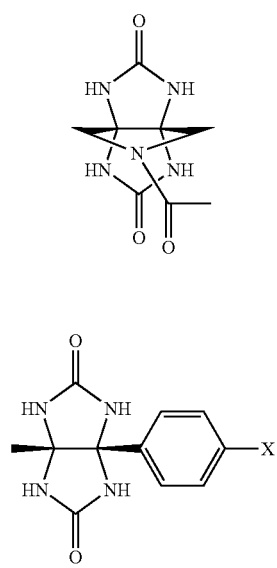

1.2
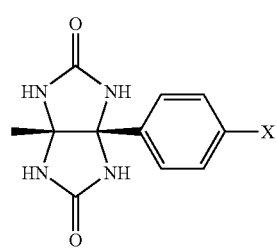

1.3
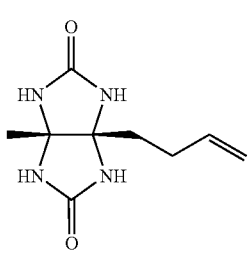

-continued 1.4
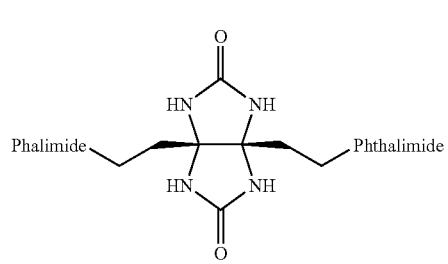

1.5
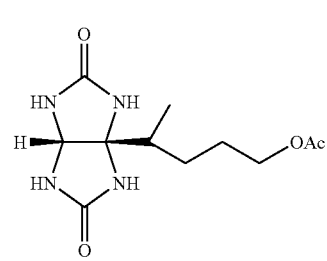

1.6
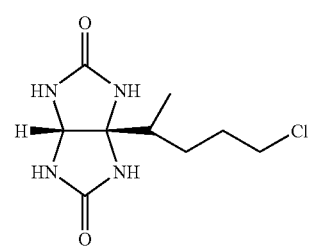

1.7
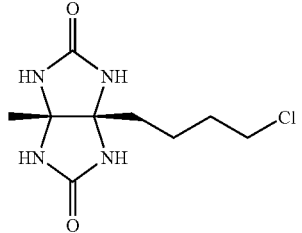

1.8
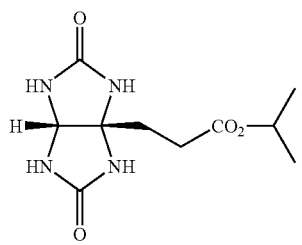

1.9
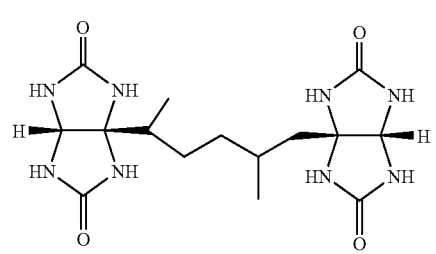

-continued

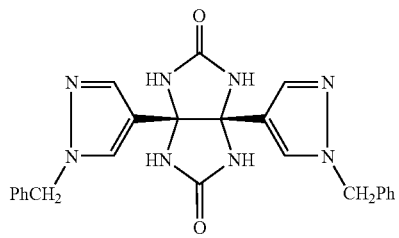

1.10

In scheme 2, the reaction to form the diamine intermediate is carried out in acid water with or without a cosolvent. The reaction of the diamine intermediate to form the glycoluril analogue is carried out under basic conditions. An example of the reaction of scheme 2 to form a glycoluril analogue where one $R^3$ group is =NH and the other $R^3$ is =O is described in I. J. Dagley and M. Kony, Heterocycles 1994, 38, 595.

Scheme 2 can for example, be used to prepare the glycoluril analogues 1.11 and 1.12.

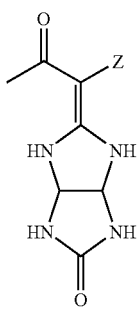

1.11 Z = CN
1.12 Z = COCH$_3$ (b) Compounds of formula (1) where $R^7$ to $R^{10}$ is not H and compounds of formula (2) where $R^{11}$ to $R^{14}$ is not H Compounds of formula (2) in which $R^{11}$ and $R^{12}$ together form the group —CHR$^5$—O—CHR$^5$— and $R^{13}$ and $R^{14}$ together form the group —CHR$^5$—O—CHR$^5$—, can be prepared by mixing a compound of formula (2) in which $R^{11}$ to $R^{14}$ are H, with trioxane, a compound of the formula $(R^5)_2$CO or a compound of the formula $R^5OC(R^5)_2OR^5$, where $R^5$ is as defined above and each $R^5$ is independently selected, and an acid, and heating the mixture to about 20° C. to 60° C. Typically, when a strong mineral acid or strong organic acid is used the mixture heated to between 20° C. to 40° C. However, if a weaker acid such as trifluoroacetic acid is used, the mixture can be heated to about 60° C.

Compounds of the formula (2) in which some or all of $R^{11}$ to $R^{14}$ are —CHR$^5$ OR$^5$ can be prepared by reacting a compound of formula (2) in which $R^{11}$ to $R^{14}$ are H with a compound of the formula XHR$^5$COR$^5$, where X is halo and each $R^5$ is independently selected and is as defined above, under basic conditions. The reaction typically occurs at room temperature, but the reaction mixture can be heated to about 40° C.

The same methods can be used to prepare compounds of formula (1) in which $R^7$ and $R^8$ together form the group —CHR$^5$—O—CHR$^5$— and $R^9$ and $R^{10}$ together form the group —CHR$^5$—O—CHR$^5$—, and compounds of formula (1) in which some or all of $R^7$ to $R^{10}$ are —CHR$^5$OR$^5$.

EXAMPLE 1

To 3a-(4-(1-chlorobutane)-6a-methylglycoluril (compound 1.7) (1 g, 4.2 mmol) suspended in 7M hydrochloric acid (1.27 mL) was added 40% formaldehyde (15 mL) and the mixture stirred at room temperature for 18 h. The resultant precipitated diether was collected by filtration washed with water and dried.

EXAMPLE 2

To 3a-(p-iodophenyl)-6a-methylglycoluril (compound 1.2 where X=I) (1 g, 1.8 mmol) dissolved in concentrated sulfuric acid (7 mL) was added 40% formaldehyde (1.7 mL) at room temperature. After 20-30 min the mixture was poured into ice water and the precipitated diether was collected by filtration and dried at 80° C. in vacuo, yield 80%.

EXAMPLE 3

To 3a,6a-diphenylglycoluril (1 g, 1.8 mmol) dissolved in concentrated sulfuric acid (7 mL) was added 40% formaldehyde (0.7 mL) at room temperature. After 20-30 min the mixture was poured into ice water and the precipitated diether was collected by filtration and dried at 80° C. in vacuo, yield 95%.

EXAMPLE 4

To 3a,6a-di(p-iodophenyl)glycoluril (1 g, 1.8 mmol) dissolved in concentrated sulfuric acid (6 mL) was added 40% formaldehyde (0.54 mL) at room temperature. After 20-30 min the mixture was poured into ice water and the precipitated diether was collected by filtration and dried at 80° C. in vacuo.

EXAMPLE 5

3a,6a-cyclopentanoglycoluril (1 g, 5.49 mmol) was added to a mixture of dimethylsufoxide (1 mL), water (2 mL) and 40% formaldehyde (1.6 mL) at room temperature and the pH of the mixture adjusted to 9 with 1 M NaOH. After 12 h the mixture was poured into methanol (15 mL) and the precipitated tetrol (compound 2.6) was collected by filtration and dried at 80° C. in vacuo 82% yield.

EXAMPLE 6

To 3a-(4-but-2-ene)-6a-methylglycoluril (compound 1.3) (1 g, 0.48 mmol) dissolved in trifluoroacetic acid (2 mL) was added 40% formaldehyde (1.46 mL) and the mixture heated to 60° C. for 12 h. Evaporation of the solvent afforded the diether, yield 70%. At short reaction times of less than 1 hr a mixture of alcohols and ethers is formed.

Diether analogues of glycoluril can also be prepared under anhydrous conditions, similar to the method of A. Wu, A. Chakraborty, D. Witt, J. Lagona, F. Damkai, M. A. Ofori, J. K. Chiles, J. C. Fettinger, and L. Isaacs J. Org. Chem. 2002, 67, 5817-5830, incorporated herein by reference.

(b) Oligomers of Formula (1) or (2)

Glycoluril analogues can be used to prepare oligomers of formula (1) and (2) comprising 2 to 11 units of formula (A) linked by bridges of the formula —CHR$^5$—. The oligomers can be prepared by mixing one or more glycoluril analogues with an acid, and if required a compound that can form bridges of the formula —CHR$^5$— between such compounds, and heating the mixture. The compound that can form bridges of the formula —CHR$^5$— may be trioxane, a compound of the formula R$^5$COR$^5$ or a compound of the formula R$^5$OC(R$^5$)$_2$OR$^5$, wherein R$^5$ is as defined above and each R$^5$ is independently selected.

The inventors have found that using suitable reaction temperatures and reaction times oligomers comprising 2 to 11 units of the formula (A) linked by bridges of the formula —CHR$^5$— can be prepared without the oligomers reacting to form cucurbiturils. Typically the oligomers are prepared by heating the reaction mixture to a temperature below 50° C. for a period of less than about 20 hours.

This process typically results in the production of a mixture of oligomers comprising different numbers of units of the formula (A). If desired, an oligomer having a particular length may be separated from the other oligomers in the mixture by crystallisation or chromatography. However, in many cases, an oligomer of one particular length is predominantly formed, and in such a case it may not be necessary to separate that oligomer from the other oligomers formed, prior to using the oligomer in the method of the present invention.

Certain compounds referred to the following examples are represented by the structures:

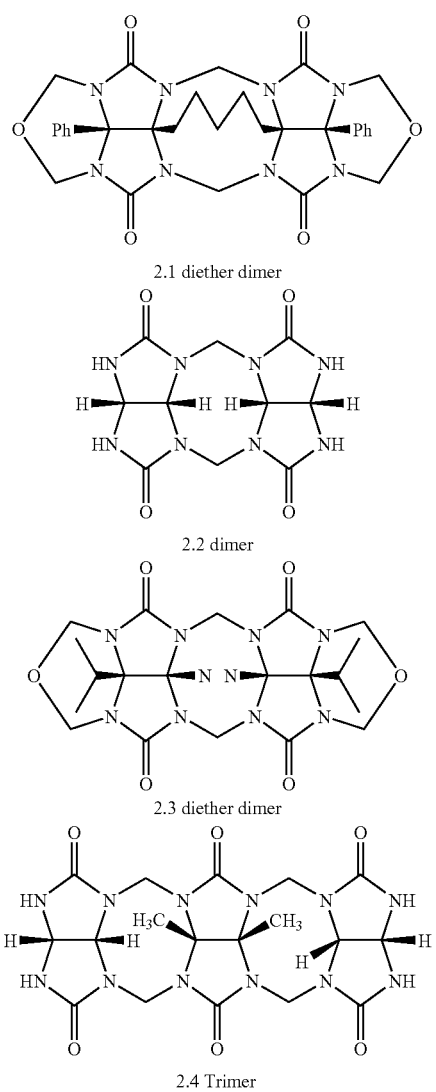

2.1 diether dimer 2.2 dimer 2.3 diether dimer 2.4 Trimer

-continued

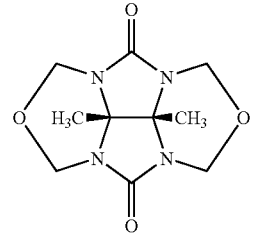

2.5 diether

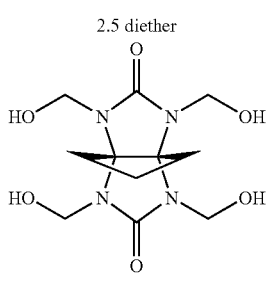

2.6 tetrol

EXAMPLE 7

To 3a-isopropylglycoluril (1 g, 5.4 mmol) dissolved in trifluoroacetic acid (15 mL) was added 40% formaldehyde (1.62 mL) and the mixture heated at 50° C. or reflux for 24 h. The solvent was evaporated to give predominantly the diether dimer (compound 2.3) which was purified or used crude.

EXAMPLE 8

To alkyltethered bisglycoluril (compound 1.9) (500 g, 1.9 mmol) dissolved in trifluoroacetic acid (15 mL) was added 40% formaldehyde (0.855 mL) and the mixture heated at 50° C. or reflux for 24 h. The solvent was evaporated to give predominantly the dimer which was purified or used crude.

EXAMPLE 9

To 3a-(4-(1-chloro-4-methylbutane)glycoluril (compound 1.6) (1 g, 4.2 mmol) dissolved in trifluoroacetic acid (15 mL) was added 40% formaldehyde (1.26 mL) and the mixture heated at 50° C. or reflux for 24 h. The solvent was evaporated to give the dimer derivative as a diether.

EXAMPLE 10

The formaldehyde diether derivative of 3a-(4-(1-chloro-4-methylbutane)glycoluril (compound 1.6) (1 g, 2.9 mmol) and the unsubstituted glycoluril dimer (compound 2.2) (1.8 g, 5.8 mmol) were mixed together in concentrated HCl (5 mL) at room temperature. After 30 mins and up to 1 hr the homogeneous mixture was poured into MeOH (10 mL) and the precipitate collected and dried to give predominantly the pentamer.

EXAMPLE 11

The formaldehyde diether derivative of 3a,6a-diphenylglycoluril (2.9 g, 7.7 mmol), the unsubstituted glycoluril dimer (compound 2.2) (4.7 g, 15.4 mmol) and K$_2$CO$_3$ (530 mg) were mixed together in methanesulfonic acid (40 mL) at room temperature, 20 min then 10 min at 50° C. The homogeneous mixture was poured into MeOH (60 mL) and the precipitate collected and dried to give predominantly the pentamer.

EXAMPLE 12

The formaldehyde diether derivative (compound 2.5) of dimethylglycoluril (1 g, 5.9 mmol) and unsubstituted glycoluril dimer (compound 2.2) (0.91 g, 2.95 mmol)in conc. HCl (2 mL) were stirred together at room temperature for 30 min to 1 hr and the homogeneous mixture was poured into MeOH (10 mL) and the precipitate collected and dried to give predominantly the diether tetramer.

EXAMPLE 13

The tetrol derivative (compound 2.6) of 3a,6a-cyclopentanoglycoluril (1 g, 3.3 mmol) was added to a solution of unsubstituted glycoluril (937 mg, 6.6 mmol) in conc. HCl (2 mL) and the mixture stirred at room temperature for 30 min. The homogeneous mixture was poured into MeOH (10 mL) and the precipitate collected and dried to give predominantly the trimer.

EXAMPLE 14

A mixture of the diether (compound 2.5) of dimethylglycoluril (1 g, 3.9 mmol), glycoluril (1.1 g, 7.75 mmol) and LiCl (250 mg) were ground together to give a fine powder. To this mixture was added 8 M HCl (10 mL) and the mixture stirred for 1 hr at ambient temperature, after which time all the solid material had dissolved. The mixture was then heat at 50° C. for 12 to 24 hr. After cooling the solvent was evacuated in vacuo. Re-crystallisation from combinations of methanol and dilute acid solutions gave the trimer (compound 2.4) 1.2 g as a pure compound.

Synthesis of Cucurbit[4 to 12]urils

EXAMPLE 15

The unsubstituted glycoluril dimer (compound 2.2) (357 mg, 1.2 mmol) and the diether (compound 2.5) of dimethylglycoluril (148 mg, 0.58 mmol) were mixed and ground together as a fine powder and added to concentrated hydrochloric acid (14 mL). The mixture was stirred at room temperature for 1 hr to form the pentamer, then paraformaldehyde (35 mg) was added and the mixture heated to 100° C. for 2-3 hr. Evaporation of the acid in vacuo gave dimethylcucurbit[1,4]uril as the major product.

EXAMPLE 16

The unsubstituted glycoluril dimer (compound 2.2) (2.36 mg, 7.7 mmol) and the diether of dimethylglycoluril (compound 2.5) (1.96 mg, 7.7 mmol) and LiCl were mixed and ground together as a fine powder and-added to concentrated hydrochloric acid (12 mL). The mixture was stirred at room temperature for 30 min. The mixture was heated to 100° C. for 2-3 hr. Evaporation of the acid in vacuo gave $\alpha$, $\delta$-tetramethylcucurbit[2,4]uril as the major product, >80%. The product was purified on Dowex cation exchange resin eluting with a mixture of formic acid and 1M HCl.

EXAMPLE 17

3a-isopropylglycoluril dimer diether (compound 2.3) (1 g, 2.5 mmol) and unsubstituted glycoluril (720 mg, 5.0 mmol) were mixed in 7M hydrochloric acid (12 mL). The mixture was stirred at room temperature for 1 hr. The mixture was heated to 100° C. for 2-3 hr. Evaporation of the acid in vacuo gave the $\alpha,\beta,\delta,\epsilon$-tetraisopropylcucurbit[4,2]uril as the major product.

EXAMPLE 18

The unsubstituted glycoluril dimer (compound 2.2) (183 mg, 0.6 mmol), the diether of butylimideglycoluril (210 g, 0.64 mmol) and p-toluenesulfonic acid (925 g) were ground together. The mixture was heated to 110° C. for 2-3 hr. Methanol was added to the hot mixture and cooled. The precipitate was collected by filtration. Purification by chromatography gave the $\alpha,\delta$-dibutylimidecucurbit[2,4]uril as the major product.

EXAMPLE 19

The unsubstituted glycoluril dimer (136 mg, 0.44 mmol), the diether of 3a-(p-iodophenyl)-6a-methylglycoluril (compound 1.2 where X=I) (264 mg, 0.62 mmol) and concentrated hydrochloric acid (1 mL) were ground together. The mixture was heated to 110° C. for 2-3 hr. Methanol was added to the hot mixture and cooled. The precipitate was collected by filtration. Purification on Sephadex SP gave the $\alpha,\delta$-di(p-iodophenyl)dimethylcucurbit[2,4]uril as the major product.

EXAMPLE 20

The unsubstituted glycoluril dimer (compound 2.2) (1 g, 3.3 mmol) and the tetrol (compound 2.6) of 3a,6a-cyclopentanoglycoluril (1 g, 3.3 mmol) were ground together as a fine powder and added to concentrated hydrochloric acid (12 mL). The mixture was stirred at room temperature for 1 hr. The mixture was heated to 100° C. for 2-3 hr. Evaporation of the acid in vacuo gave $\beta,\delta$-dicyclopentanocucurbit[2,4]uril as the major product, 80%.

EXAMPLE 21

The unsubstituted glycoluril dimer (compound 2.2) (135 mg, 0.44 mmol and LiCl (9 mg) were added to conc HCl (10 mL) and stirred at room temperature for 20 min. A mixture of the diether (compound 2.5) of dimethylglycoluril (55.9 mg, 0.22 mmol) and the diether (compound 1.2 where X=H) of 3a-phenyl-6a-methylglycoluril (140 mg, 0.22 mmol) ground together as a homogeneous solid, were added to the mixture. After an initial period of 20 min at room temperature the mixture was heated to 100° C. for 3 hr. Evaporation of the acid in vacuo gave $\alpha$-phenyl-$\alpha$-methyl-$\delta$-dimethylcucurbit[2,4]uril as the major product.

EXAMPLE 22

The formaldehyde diether derivative of 3a,6a-diphenylglycoluril (2.9 g, 7.7 mmol), the unsubstituted glycoluril dimer (compound 2.2) (4.7 g, 15.4 mmol) and $K_2CO_3$ (530 mg) were mixed together in methanesulfonic acid (40 mL) at room temperature, 20 min then 10 min at 50° C. Then paraformaldehyde (460 mg) was added and the mixture heated to 100° C. for 2.5 hr. The cooled homogeneous mixture was poured into MeOH (170 mL) and the product collected by filtration washed MeOH and dried to give 7.6 g of product mixture, predominantly diphenylcucurbit[1,4]uril.

EXAMPLE 23

A mixture of compound 1.12 (500 mg, 2.2 mmol) and paraformaldehyde (295 mg) was heated under reflux in trifluoroacetic acid (10 mL) for several hours. The product obtained by evaporation of the solvent was used without purification. The product was mixed with the glycoluril dimer (compound 2.2) (670 mg) and 7M HCl (15 mL) was added at ambient temperature. After 30 min the mixture was heated to 90° C. for 3 h. The mixture was then cooled and methanol added to precipitate the product. $^1$H NMR showed characteristic cucurbituril proton resonances as groups of doublets at 4.1 and 5.1 ppm, in addition the methyl proton resonances were evident at 2.3 ppm. Dioxane binding showed that a cucurbit[6]uril had been formed. The cucurbit[6]uril contained some units of the formula (B) in which one of the $R^3$ groups is $=C(COCH_3)_2$.

EXAMPLE 24

A mixture of glycoluril dimer (compound 2.2) (1.2 g, 3.9 mmol), the diether (compound 2.5) of dimethylglycoluril (1 g, 3.9 mmol) and LiCl (250 mg) were ground together to give a fine powder. To this mixture was added concentrated HCl (10 ml) and the mixture stirred at ambient temperature for 1 hr. To this mixture was added the trimer compound 2.4 (1.95 g, 3.9 mmol) and stirring continued for an additional hr. The mixture was then heat to 100° C. for 3 hr. The solvent was evaporated in vacuo to give a solid residue, which was purified on Dowex cation exchange resin. Alpha, gamma, zeta-hexamethylcucurbit[3,4]uril was isolated as a crystalline solid 1.1 g.

The present invention can be used to prepare cucurbiturils having particular $R^1$, $R^2$, $R^3$ and $R^5$ groups at particular relative locations in the units of the formula (B) making up the cucurbituril. This allows the preparation of cucurbiturils having suitable solubility and complexing properties for the intended use of the cucurbituril, or having particular numbers and relative locations of substituents for reaction with other compounds.

As is apparent from the above examples, the method of the present invention can produce good yields of specific cucurbiturils, including specific variably substituted cucurbiturils. The prior art methods for producing a variably substituted cucurbituril typically result in the production of a large number of different cucurbiturils, and thus typically low yields of the desired variably substituted cucurbituril.

In some embodiments of the present invention, the method of the present invention produces a mixture of different cucurbiturils. If required, individual cucurbit[4 to 12]urils prepared by the method of the present invention may be separated from any other cucurbit[4 to 12]urils produced by the reaction, by the separation methods described in WO 00/68232.

The potential uses for cucurbit[n]urils prepared by the method of the present invention are large, with academic, industrial, analytical and pharmaceutical applications. As a class, cucurbit[n]urils can be favourable compared to the cyclodextrins because both molecular systems possess a hydrophobic cavity with polar end caps. Cucurbiturils are however thermally more robust than cyclodextrins and are stable to strong acid solutions unlike cyclodextrins. Cyclodextrins have been used in a wide range of applications including slow release drugs, odour entrapment agents in plastic films, and enzimimics for synthesis. It is believed that cucurbit[n]urils will be of use in similar areas where benefit can be taken of the ability of the cucurbit[n]urils to take up molecules or compounds into their central cavity or bind molecules at the polar ends of the cavity. Such uses include:

Environmental (Water, Soil and Air)
  Remediation, by the binding of polluting products and their removal.
  Preventative, e.g. by binding of potential pollutants before wastes are released to the environment.
  Uses in biodegradable polymers.

Domestic and Public
  Incorporation into polymers as odourisers, releasing fragrances slowly over time.
  Incorporated into polymers to trap unpleasant odours or toxic vapours.
  Encapsulation of bleaching and whitening agents.

Food
  Flavour enhancers.
  Flavour optimisers (hiding unpleasant flavours).
  Polyphenol removal to reduce discolouration of juices.

Pharmaceutical
  Slow release drugs, limiting side effects and reducing the frequency of doses.
  Increasing drug stability in vivo or on the shelf.
  Detoxification, for example,. decreasing stomach irritations, or the treatment of chemical allergens by encapsulation.

Agricultural/Horticultural
  Slow release of herbicides and pesticides.
  Stablisation of agricultural chemicals against light and heat.

Manufacturing
  Enzyme/catalyst mimics.
  Regioselective control over reaction products.
  Manipulation of paint and polymer products.
  Chromatographic columns for chemical purification.
  Analytical tools and devices.
  Printing and photography.

Those skilled in the art will appreciate that the invention described herein may be susceptible to variation and modifications other than those specifically described or exemplified. It is to be understood that the present invention encompasses all such variations and modifications that fall within its spirit and scope.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.ss

The invention claimed is:

1. A method for preparing a cucurbituril, the method comprising the steps of:
  (a) selecting
    (1) a compound of the formula (1)

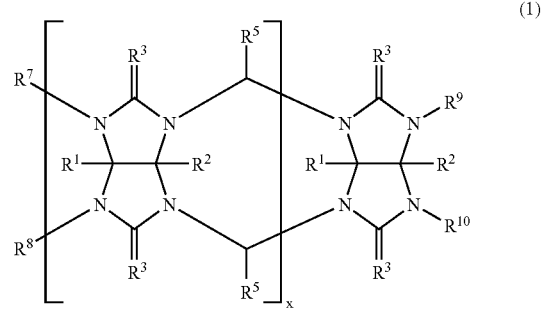

wherein:

for each unit of the formula (A)

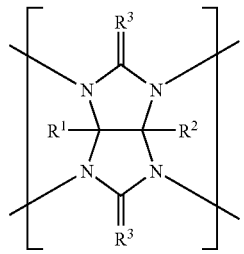

in the compound,

R¹ and R² may be the same or different and are each a univalent radical, or

R¹, R² and the carbon atoms to which they are bound together form an optionally substituted cyclic group, or R¹ of one unit of the formula (A) and R² of an adjacent unit of the formula (A) together form a bond or a divalent radical, and each R³ is independently selected from the group consisting of =O, =S, =NR, =CXZ, =CRZ and =CZ$_2$, where Z is an electron withdrawing group, X is halo and R is H, an optionally substituted straight chain, branched or cyclic, saturated or unsaturated hydrocarbon radical, or an optionally substituted heterocyclyl radical;

each R⁵ is independently selected from the group consisting of H, alkyl and aryl;

R⁷ and R⁸ may be the same or different and are independently selected from the group consisting of H and —CHR⁵OR⁵, or R⁷ and R⁸ together form the group —CHR⁵—O—CHR⁵, where each R⁵ is independently selected from the group consisting of H, alkyl and aryl;

R⁹ and R¹⁰ may be the same or different and are independently selected from the group consisting of H and —CHR⁵OR⁵, or R⁹ and R¹⁰ together form the group —CHR⁵—O—CHR⁵, where each R⁵ is independently selected from the group consisting of H, alkyl and aryl; and x is an integer from 1 to 10; and (2) one or more compounds of the formula (2)

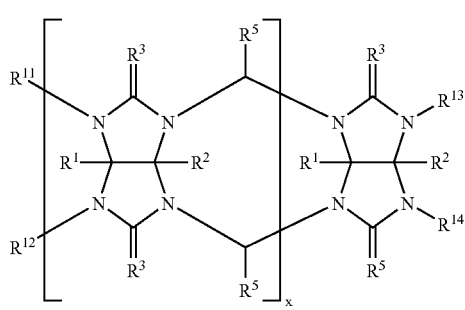

wherein:

for each unit of the formula (A)

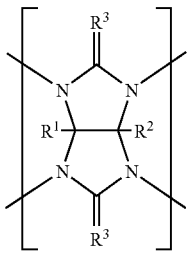

in the compound,

R¹ and R² may be the same or different and are each a univalent radical, or

R¹, R² and the carbon atoms to which they are bound together form an optionally substituted cyclic group, or R¹ of one unit of the formula (A) and R² of an adjacent unit of the formula (A) together form a bond or a divalent radical, and each R³ is independently selected from the group consisting of =O, =S, =NR, =CXZ, =CRZ and =CZ$_2$, where Z is an electron withdrawing group, X is halo and R is H, an optionally substituted straight chain, branched or cyclic, saturated or unsaturated hydrocarbon radical, or an optionally substituted heterocyclyl radical;

each R⁵ is independently selected from the group consisting of H, alkyl and aryl;

R¹¹ and R¹² may be the same or different and are independently selected from the group consisting of H and —CHR⁵OR⁵, or R¹¹ and R¹² together form the group —CHR⁵—O—CHR⁵—, where each R⁵ is independently selected from the group consisting of H, alkyl and aryl;

R¹³ and R¹⁴ may be the same or different and are independently selected from the group consisting of H and —CHR⁵OR⁵, or R¹³ and R¹⁴ together form the group —CHR⁵—O—CHR⁵—, where each R⁵ is independently selected from the group consisting of H, alkyl and aryl; and y is 0 or an integer from 1 to 9 and x+y=10 or less;

(b) mixing the compound of formula (1), the one or more compounds of formula (2) and an acid to form a mixture; and (c) exposing the mixture to conditions effective for the compound of the formula (1) and the one or more compounds of the formula (2) to form a cucurbit[n]uril.

2. A method according to claim 1 wherein R¹ and R² are independently selected from the group consisting of —R, —OR, —N$_2$ where each R is independently selected, —NO$_2$, —CN, —X, —COR, —COX, —COOR,

where each R is independently selected,

where each R is independently selected, —SeR, —SiR$_3$ where each R is independently selected, —SR, —SOR,

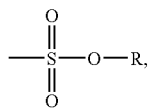

—SO$_2$R, —S—S—R, —BR$_2$ where each R independently selected, —PR$_2$ where each R is independently selected,

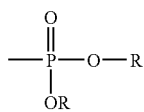

where each R is independently selected,

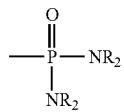

where each R is independently selected, —P$^+$R$_2$ where each R is independently selected and a metal or metal complex, wherein R is H, an optionally substituted straight chain, branched or cyclic, saturated or unsaturated hydrocarbon radical, or an optionally substituted heterocyclyl radical, and X is halo.

3. A method according to claim 2 wherein R is H, an optionally substituted C$_{1-10}$ alkyl, an optionally substituted C$_{2-10}$ alkenyl, or an optionally substituted C$_{5-10}$ aryl.

4. A method according to claim 1 wherein the mixture further comprises one or more compounds that can form bridges of the formula —CHR$^5$— between compounds of formula (1) and (2).

5. A method according to claim 4 wherein the compound that can form bridges of the formula —CHR$^5$— between compounds of formula (1) and (2) is selected from the group consisting of trioxane, optionally substituted 2,3-dihydropyran, optionally substituted 2,3-dihydrofuran, compounds of the formula R$^5$COR$^5$ and compounds of the formula R$^5$OC(R$^5$)$_2$OR$^5$, where each R$^5$ is independently selected and is H, alkyl or aryl.

6. A method according claim 5 wherein the compound that can form bridges of the formula —CHR$^5$— between compounds of formula (1) and (2) is formaldehyde, paraformaldehyde or trioxane.

7. A method according to claim 1 wherein step (c) comprises heating the mixture to a temperature of from 20° C. to 120°C. for a period of time sufficient for the compound of formula (1) and the one or more compounds of formula (2) to form a cucurbit[n]uril.

8. A method according to claim 1 wherein R$^7$=R$^8$, R$^9$=R$^{10}$, R$^{11}$=R$^{12}$ and R$^{13}$=R$^{14}$.

9. A method according to claim 1 wherein Z is selected from the group consisting of —NO$_2$, —CO$_2$R, —COR, —CN and —CX$_3$, where X is halo and R is H, alkyl, alkenyl, alkynyl, aryl, or saturated or unsaturated heterocyclyl.

10. A method according to claim 1 wherein R$^3$ is =O.

11. A method according to claim 1 wherein R$^5$ is H.

12. A method according to claim 1 wherein the mixture further comprises a templating compound.

13. A method according to claim 12 wherein the templating compound is a salt.

14. A method according to claim 13 wherein the anion of the salt corresponds to the anion of the acid in the mixture.

15. A method according to claim 12 wherein the templating compound is selected from ammonium chloride, lithium chloride, sodium chloride, potassium chloride, rubidium chloride, caesium chloride, ammonium bromide, lithium bromide, sodium bromide, potassium bromide, rubidium bromide, caesium bromide, lithium iodide, sodium iodide, potassium iodide, rubidium iodide, caesium iodide, potassium sulfate, lithium sulfate, tetrabutylammonium chloride, tetraethylammonium chloride, o-carborane, thioacetamide, N-(1-napthyl) ethylenediamine, 2,2'-biquinoline, p-bromoanaline, taurine, blue tetrazolium, 2-amino3-methyl benzoic acid, indol-3-aldehyde, cysteine, 4-acetamidoaniline, p-aminophenol, acetamide, 4-aminoacetophenone, 4-dimethylaminobezaldehyde, 2-aminobenzimidazol, bis-(4,4'-bipyridyl)-α,α'-xylene, red phosphorus, and lithium p-toluenesulfonate.

16. The method of claim 15, wherein the templating compound is 4-dimethylaminobezaldehyde.

17. The method of claim 1, wherein the acid is selected from the group consisting of sulfuric acid, hydrochloric acid, hydrobromic acid, hydriodic acid, deuterated sulfuric acid, phosphoric acid, p-toluenesulfonic acid and methane sulphonic acid.

* * * * *

UNITED STATES PATENT AND TRADEMARK OFFICE
CERTIFICATE OF CORRECTION

PATENT NO. : 7,501,523 B2  Page 1 of 1
APPLICATION NO. : 10/571707
DATED : March 10, 2009
INVENTOR(S) : Day et al.

It is certified that error appears in the above-identified patent and that said Letters Patent is hereby corrected as shown below:

In the Claims section please make the following corrections:

In claim 1 at column 26, line 47, change [cucurbituril] to -- cucurbit[n]uril --

In claim 1 at column 27, line 5, please insert -- (A) -- to the right of the formula In claim 2 at column 28, line 59, change [-N$_2$] to -- -NR$_2$ --

In claim 15 at column 30, line 38, change [2-amino3-methyl] to -- 2-amino-3-methyl --

Signed and Sealed this

Twenty-seventh Day of October, 2009

David J. Kappos
*Director of the United States Patent and Trademark Office*